United States Patent
Chin

Patent Number: 6,115,621
Date of Patent: Sep. 5, 2000

[54] OXIMETRY SENSOR WITH OFFSET EMITTERS AND DETECTOR

[75] Inventor: Rodney P. Chin, Oakland, Calif.

[73] Assignee: Nellcor Puritan Bennett Incorporated, Pleasanton, Calif.

[21] Appl. No.: 08/903,120

[22] Filed: Jul. 30, 1997

[51] Int. Cl.[7] .................................................. A61B 5/00
[52] U.S. Cl. ........................................ 600/323; 600/344
[58] Field of Search .................................. 600/310–344, 600/473, 475, 476, 477

[56] References Cited

U.S. PATENT DOCUMENTS

| | | |
|---|---|---|
| Re. 33,643 | 7/1991 | Isaacson et al. . |
| 4,086,915 | 5/1978 | Kofsky et al. . |
| 4,167,331 | 9/1979 | Nielsen . |
| 4,266,554 | 5/1981 | Hamaguri .............................. 128/633 |
| 4,407,290 | 10/1983 | Wilber . |
| 4,463,764 | 8/1984 | Anderson et al. . |
| 4,586,513 | 5/1986 | Hamaguri . |
| 4,623,248 | 11/1986 | Sperinde . |
| 4,700,708 | 10/1987 | New, Jr. et al. . |
| 4,714,080 | 12/1987 | Edgar, Jr. et al. . |
| 4,714,341 | 12/1987 | Hamaguri et al. . |
| 4,784,150 | 11/1988 | Voorhies et al. . |
| 4,796,636 | 1/1989 | Branstetter et al. . |
| 4,805,623 | 2/1989 | Jöbsis . |
| 4,807,631 | 2/1989 | Hersh et al. . |
| 4,819,752 | 4/1989 | Zeliin . |
| 4,822,568 | 4/1989 | Tomita . |
| 4,824,242 | 4/1989 | Frick et al. . |
| 4,869,253 | 9/1989 | Craig, Jr. et al. . |
| 4,869,254 | 9/1989 | Stone et al. . |
| 4,928,692 | 5/1990 | Goodman et al. . |
| 5,028,787 | 7/1991 | Rosenthal et al. . |
| 5,048,524 | 9/1991 | Bailey . |
| 5,119,815 | 6/1992 | Chance . |
| 5,188,108 | 2/1993 | Secker . |
| 5,213,099 | 5/1993 | Tripp, Jr. . |
| 5,219,400 | 6/1993 | Jacot et al. . |
| 5,246,002 | 9/1993 | Prosser . |
| 5,259,381 | 11/1993 | Cheung et al. . |
| 5,300,769 | 4/1994 | Dahlin et al. . |
| 5,313,940 | 5/1994 | Fuse et al. . |
| 5,348,004 | 9/1994 | Hollub . |
| 5,351,685 | 10/1994 | Potratz . |
| 5,355,882 | 10/1994 | Ukawa et al. . |
| 5,368,224 | 11/1994 | Richardson et al. . |
| 5,372,134 | 12/1994 | Richardson . |
| 5,379,238 | 1/1995 | Stark . |
| 5,408,998 | 4/1995 | Mersch . |
| 5,413,101 | 5/1995 | Sugiura . |
| 5,490,523 | 2/1996 | Isaacson et al. . |
| 5,503,148 | 4/1996 | Pologe et al. . |
| 5,551,422 | 9/1996 | Simonsen et al. ...................... 600/476 |
| 5,551,423 | 9/1996 | Sugiura . |
| 5,596,986 | 1/1997 | Goldfarb . |
| 5,770,454 | 6/1998 | Essenpreis et al. ..................... 600/310 |
| 5,800,349 | 9/1998 | Isaacson et al. . |
| 5,817,008 | 10/1998 | Rafert et al. ............................ 600/310 |

FOREIGN PATENT DOCUMENTS

WO 95/32416  11/1995  Germany ............................... 600/476

*Primary Examiner*—John P. Leubecker
*Assistant Examiner*—David M. Ruddy
*Attorney, Agent, or Firm*—Townsend and Townsend and Crew LLP

[57] ABSTRACT

An improved oximeter sensor structure for attaching to an appendage of a patient. The emitters and the detector are offset from each other, so that they are not directly opposite each other. This causes the light emitted by the emitters to pass through more blood-perfused tissue to reach the detector than it would on the direct path through the appendage if the emitters and detector were opposite each other.

21 Claims, 2 Drawing Sheets

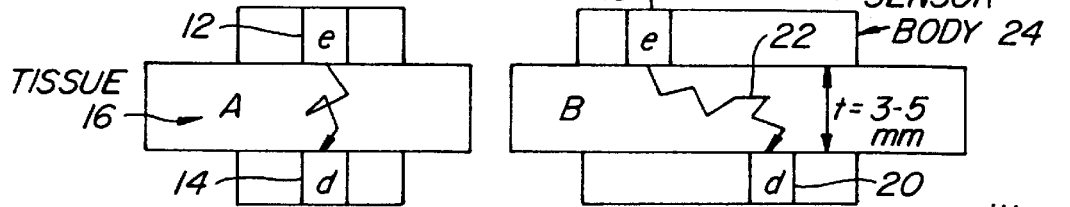
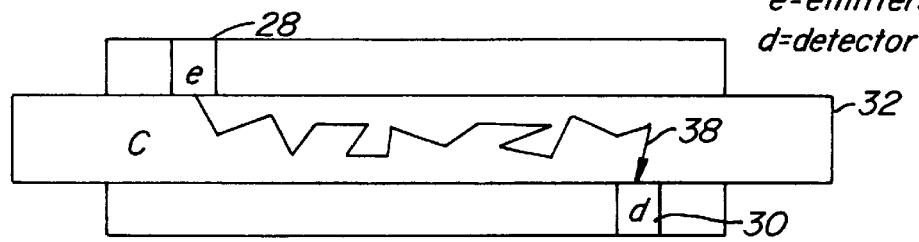
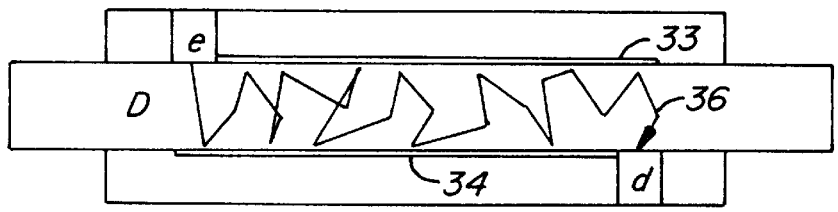
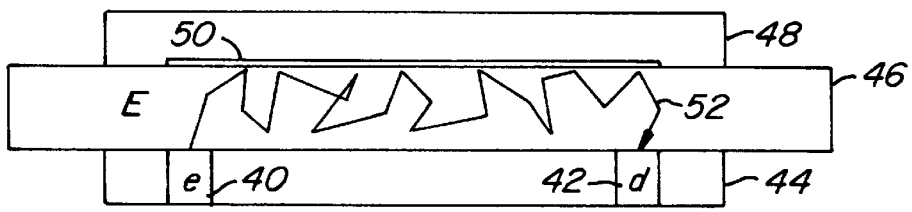
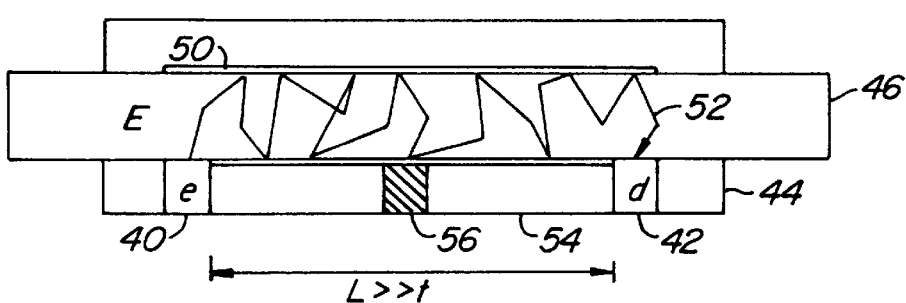
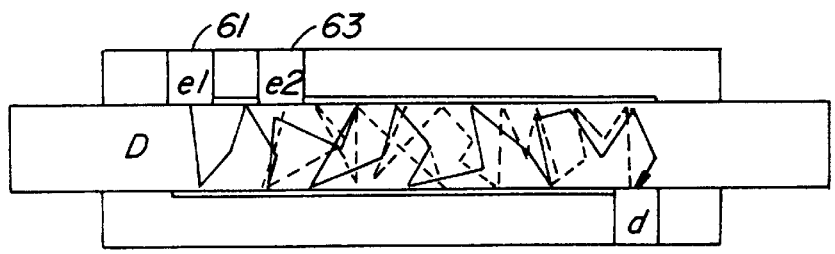

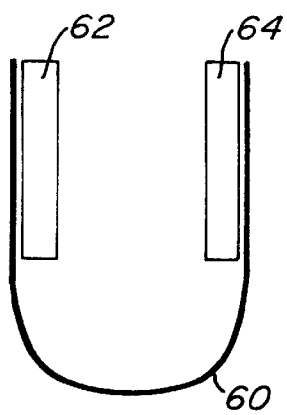
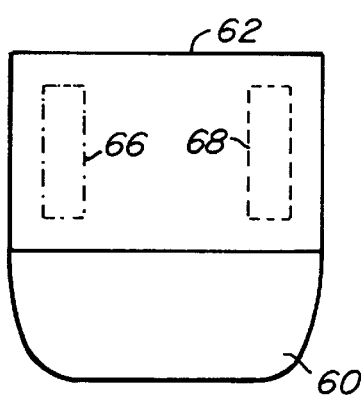
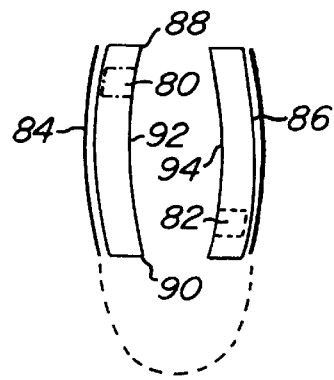
FIG. 2A.  FIG. 2B.  FIG. 4.
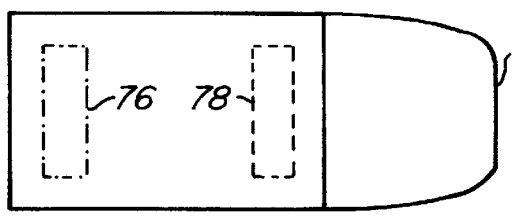
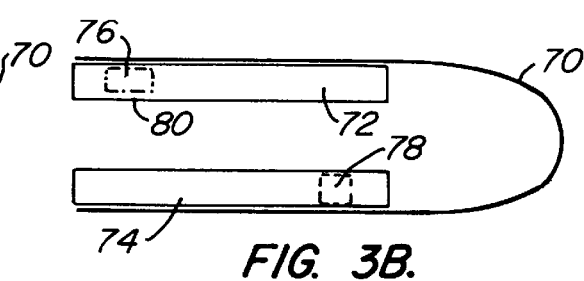
FIG. 3A.  FIG. 3B.
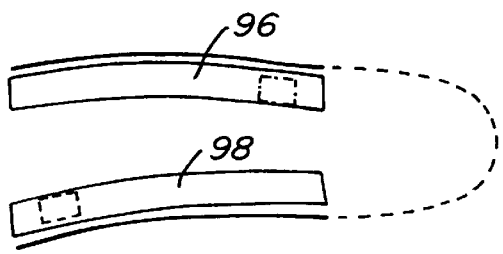
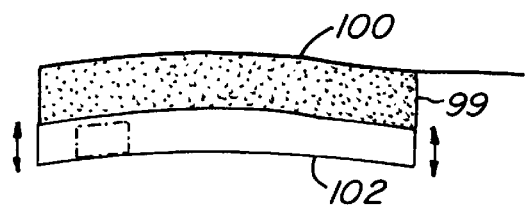
FIG. 5.  FIG. 6.

1

OXIMETRY SENSOR WITH OFFSET EMITTERS AND DETECTOR

BACKGROUND OF THE INVENTION

The present invention relates to oximetry sensors, and in particular to pulse oximetry sensors which attach across a patient's appendage.

Pulse oximeter sensors are often attached to a digit, or ear. These sites on a patient provide an adequate level of blood perfusion for measuring the oxygenation of the blood hemoglobin. In addition, the distance across these appendages is sufficiently short to allow the detection of transmitted red or infrared light.

One type of sensor is a clothespin-type clip which attaches across the earlobe, with the emitter and detector opposite each other. Such conventional sensors sometime suffer from poor sensitivity and poor calibration or accuracy.

This type of sensor often applies pressure which exsanguinates the tissue and alters the blood present leading to accuracy errors.

One type of oximeter sensor will add a diffusing optic to diffuse the light emitted from the light-emitting diodes (LEDs) to cause it to pass through more tissue, and thus more blood. An example of a pulse oximeter sensor using such a diffusing element is shown in U.S. Pat. No. 4,407,290.

One technique for limiting the exsanguination effect is to separate the light emitters and detector from the portion of the sensor which holds it to the appendage and applies the pressure. Examples of sensors where the light emitters and detector avoid the point of pressure are set forth in U.S. Pat. Nos. 5,413,101 and 5,551,422.

Another type of clip-on sensor is marketed by Nonin Medical, Inc. for attaching to an ear. Instead of using a transmission sensor where light is transmitted from an emitter on one side of the ear through the ear to a detector on the other side, a reflectance sensor is used with both the emitter and detector on the same side of the ear. The Nonin medical sensor has spacing between the emitter and the detector of approximately 4 mm, which is similar to the thickness of a typical earlobe. On the opposite side of the ear a reflective surface is provided to reflect the light from the emitter back to the detector.

The typical distance of a standard, band-aid-type reflectance sensor which can attach to the forehead or other part of the body is 6–10 mm. Traditionally, a spacing of this magnitude was felt to be appropriate to ensure that a measurable amount of light could be detected with sufficient pulsatile signal components.

SUMMARY OF THE INVENTION

The present invention provides an improved oximeter sensor structure for attaching to an appendage of a patient. The emitters and the detector are offset from each other, so that they are not directly opposite each other. This causes the light emitted by the emitters to pass through more blood-perfused tissue to reach the detector than it would on the direct path through the appendage if the emitters and detector were opposite each other.

In a preferred embodiment, the sensor includes at least one reflecting surface for redirecting light back to the blood-perfused tissue in the region of the offset between the emitters and detector. Preferably, the offset distance is at least greater than, and more preferably at least twice as great as, the direct, shortest path through the appendage.

In an alternate embodiment, a reflectance-type sensor is used, with a reflective surface on the opposite side of the appendage. Unlike the prior art, however, the distance between the emitter and detector is greater than, and preferably twice as great as, the shortest, direct distance through the appendage.

For a further understanding of the nature and advantages of the invention, reference should be made to the following description taken in conjunction with the accompanying drawings.

BRIEF DESCRIPTION OF THE DRAWINGS

FIG. 1A is a diagram of a prior art emitter and detector configuration.

FIGS. 1B–1G are diagrams of different embodiments of the configuration of the emitter and detector according to the invention.

FIGS. 2A and 2B are end and side views of an ear sensor according to the invention.

FIGS. 3A and 3B are side and top views of a nostril sensor according to the invention.

FIGS. 4 and 5 are diagrams of alternate embodiments illustrating curves in the sensor.

FIG. 6 is a diagram of a sensor with foam for distributing applied pressure.

DESCRIPTION OF THE PREFERRED EMBODIMENT

FIG. 1A illustrates a prior art configuration in which an emitter 12 is opposite a detector 14 across an earlobe, nostril, digit, or other appendage 16.

FIG. 1B illustrates an offset configuration in which an emitter 18 is offset from a detector 20 as can been seen, providing a longer light transmission path 22. Emitter 18 is typically a pair of emitters, an infrared range emitter and a red range emitter, which are mounted in a portion 24 of a sensor probe. Detector 20 is a photodetector which is mounted in a portion 26 of a sensor probe.

FIG. 1C illustrates an alternate embodiment in which emitter 28 is spaced from a detector 30 by an offset distance which is more than twice the width of appendage 32. As can be seen, this provides a much longer transmission path 38.

FIG. 1D illustrates an embodiment similar to FIG. 1C, where a pair of reflectors 33 and 34 have been added. As can be seen, the reflectors 33 and 34 cause the light path 36 in FIG. 1D to be longer than the light path 38 in FIG. 1C. This is due to light which goes across the entire appendage being reflected back in, and then back in from the other surface, bouncing back and forth between the reflectors until it reaches the detector from the emitter. In FIG. 1C, by contrast, the light which reaches the detector from the emitter is substantially the light which moves in a path through the body of the appendage, since light which would hit the edges would typically be absorbed, rather than being reflected.

The reflective surface 33 may be, for instance, a white surface which will reflect both red and infrared light. This will enhance the path length of both red and infrared light. Alternatively, the reflective surface 33 may be "colored" to reflect red light more than infrared light (or vice versa) to compensate for skin pigmentation effects.

FIGS. 1E and 1F show alternate embodiments in which the emitter and detector are on the same side of the appendage in a reflectance configuration. As shown in FIG. 1E, an emitter 40 and a detector 42 are in a portion 44 of a sensor attached to an appendage 46, such as an earlobe. The sensor, which may be a clip-on type sensor, has a second portion 48 opposite portion 44. Portion 48 includes a reflective surface 50. As can be seen, the light path 52 will thus be reflected back from surface 50, providing more light to detector 42 than would be found in a typical reflectance configuration. (Please note that the light path shown in these figures is merely illustrative). The use of reflector 50 allows not only more light to be directed back into the tissue to arrive at detector 42, but allows a larger space between emitter 40 and detector 42. As in FIGS. 1C and 1D, the distance L between the emitter and detector in FIG. 1E is preferably greater than the width t of the appendage, and preferably a value of L which is at least twice t.

FIG. 1F shows an alternate embodiment to that of FIG. 1E in which a second reflector 54 is added between the emitter 40 and detector 42 in portion 44 of the sensor probe. This prevents the light from being absorbed in the body of the sensor 44 between emitter 40 and detector 42 on the same side. A reflector on one side will improve performance over a sensor without such a reflector, while a reflector on both sides would typically give even more enhanced performance. However, even a single reflector provides a significant improvement in the amount of light reaching the detector.

Also shown in FIG. 1F is a shunt barrier 56. Shunt barrier 56 prevents light from shunting directly between emitter 40 and detector 42 through sensor body 44 without passing through appendage 46. Examples of shunt barriers are set forth in commonly-owned copending application entitled SHUNT BARRIER IN PULSE OXIMETER SENSOR, Application No. 08/611,151, filed Mar. 5, 1996.

FIG. 1G shows an alternate embodiment in which two emitters, 61 and 63, have a different offset distance from the detector. This can be used to partially compensate for a difference in absorption of red and infrared.

FIG. 2A shows an end view of one embodiment of an ear clip sensor according to the present invention. Other embodiments are possible, but this embodiment shows a simple, inexpensive, disposable-type sensor. A bent piece of metal 60 holds pads 62 and 64, which contain the light emitters and detector, respectively. Bent metal 60 is springy to provide pressure applying the pads 62, 64 against the earlobe. The pads (62 and 64) are rigid since the earlobe conforms easily. Preferably, slowly deformable spring material is used, which is an assembly which provides the gripping action but has a damping component which prevents quick movements. (e.q., metal sheet as the spring with a rubber coating of laminate).

In the side view of FIG. 2B, pad 62 is shown, along with the position of an emitter 66. Shown in phantom is the position on the other pad where detector 68 would be located.

FIGS. 3A and 3B show a similar configuration for a nostril sensor, which is basically more slender and narrow. As shown in FIG. 3B, a bent metal 70 provides the springiness for pads 72 and 74. Pad 72 includes an emitter 76, while pad 74 includes a detector 78. Also shown is an optional optical diffuser 80 for diffusing the light from emitter 76, which causes a further spreading or mixing of light and may enhance the amount of tissue penetrated in some instances.

FIG. 3A shows a side view with the relative position of emitter 76 and detector 78 shown in phantom.

FIG. 4 illustrates an exaggerated view of the construction of one embodiment of the sensor of FIGS. 2A, 2B, 3A and 3B. In the view of FIG. 4, an emitter 80 and detector 82 are shown.

Emitter 80 is mounted on the edge of a curved portion 84 of one end of the sensor, while detector 82 is mounted near the end of a curved portion 86 on the other side of the sensor. The curvature in FIG. 4 would range from zero (no curvature) to less than 15% depth of offset distance or to less than 30% depth of offset distance. These curved portions ensure that less pressure will be applied to the appendage in-between the emitter and detector. Instead, more pressure is applied, for instance, to points 88 and 90, which are outside of the region in-between the emitter and detector. Thus, this configuration reduces the exsanguination of the tissue in-between the emitter and detector. It is desirable that some pressure is applied throughout to reduce the amount of venous pooling in the tissue.

Preferably, the spring force of the metal clip in the embodiments of FIGS. 2–6 has sufficient pressure so that it exceeds the typical venous pressure of a patient, but does not exceed the diastolic arterial pressure. The signal received by the detector will include both a DC component and an AC component. The AC and DC components are monitored to determine variations in the oxygen saturation. By having a pressure greater than the venous pressure, contributions to the AC waveform from the venous blood are limited, thus enhancing the sensitivity to variations in the arterial blood pressure. Since the pressure of the clip is less than that of the arterial pressure, it does not inhibit the arterial AC signal significantly.

The pressure applied to the spring is such that the pressure exerted on the tissue is equal to the force applied by the spring divided by the contact area to the tissue. Since the system is in steady state, the compressed tissue will be at a minimum pressure exerted by the contact surfaces.

Typical venous pressure, diastolic and systolic arterial pressures are <10–35 mmHg, 80 mmHg, and 120 mmHg, respectively. Functionally, these vary due to the location of the vascular bed and the patient's condition. Low arterial diastolic blood pressure (~30 mmHg) may occur in sick patients. The sensor would/could be adjusted for an average pressure of 15–30 mmHg. It is more desirable to be a little low. Removal of most venous pooling would occur with light to moderate pressure (~15 mmHg). This would give the most enhancement of the pulse modulation by removing unnecessary DC (non-pulsatile) absorption by the blood.

The sensor's pressure may be adjusted by mechanical means to optimize for the best pulse modulation.

In a preferred embodiment, adhesives 92 and 94 are applied to the interior surface of the clip sensor in FIG. 4 to enhance the securing of the sensor to the appendage. Preferably, this is done in combination with a slight curve of the sensor (which is exaggerated in FIG. 4). The use of an adhesive improves the contact of the sensor to the appendage, and limits the susceptibility to motion artifact which might vary the distance or degree of contact between the sensor and the appendage. In addition, due to the curved shape, the likelihood of a gap between the sensor body and the skin is avoided. If the adhesive is thin enough or black, it will not shunt appreciably.

FIG. 5 illustrates a sensor with concave and convex surfaces 96 and 98. The particular curvature can be matched to the desired patient site. FIG. 6 illustrates the addition of a foam 99 between a sensor spring 100 and a pad 102. Foam 99 can help distribute the pressure from the spring.

The present invention provides a number of advantages. The cardiac pulse modulation or AC portion of the detected signal, has been observed in experiments to be increased by greater than three times (providing greater than 1% IR modulation of the DC signal at 100% SpO2). This increased AC cardiac signal level is believed to be due to the longer absorption path length. The increased AC cardiac signal amplitude allows it to be more easily processed by the oximeter electronics and software. In addition, the increased AC cardiac modulation level limits the sensor's susceptibility to noise due to either motion artifact or EMI interference.

The present invention also provides more stable DC levels. The path length is dominated by the offset distance rather than the tissue thickness since the offset distance is much greater. This offset distance for any one particular sensor is consistent from patient to patient. In addition, the increased distance between the emitter and detector limits the amount of direct optical shunting through the tissue, thus further limiting the corrupting effect on the DC level.

As will be understood by those of skill in the art, the present invention may be embodied in other specific forms without departing from the spirit or essential characteristics thereof. Accordingly, the foregoing example is meant to be illustrative, but not limiting, of the scope of the invention which is set forth in the following claims.

What is claimed is:

1. An oximeter sensor comprising:
   a first member configured to contact a first side of a tissue region of a patient;
   at least one emitter mounted in said first member;
   at least one detector mounted to contact said tissue region on a second side;
   an attachment structure configured to attach said sensor to said tissue region so that said detector is offset from a shortest path through said tissue region from said emitter; and
   a first diffuse or specular reflecting surface mounted to attach to said tissue region in a region of said offset.

2. The oximeter sensor of claim 1 wherein said first reflective surface only partially covers said offset region.

3. The oximeter sensor of claim 1 wherein said offset is greater than said shortest path through said tissue region.

4. The oximeter sensor of claim 1 wherein said offset is more than twice said shortest path.

5. The oximeter sensor of claim 1 wherein said attachment structure comprises a spring loaded U-shaped metal or plastic clip, said first member being a first end of said clip.

6. The oximeter sensor of claim 1 wherein said first member and said attachment structure comprise a flexible substrate, and further comprising an adhesive for attaching said flexible substrate to said tissue region.

7. The oximeter sensor of claim 1 wherein said attachment structure is configured to apply a pressure to said tissue region between said emitter and said detector which is between a venous and a diastolic arterial pressure of said patient in said tissue region.

8. The oximeter sensor of claim 1 wherein at least one of said attachment structure and said members are configured to apply less pressure to said tissue region in a first region between said emitter and said detector than a pressure applied to a second region of said tissue region outside said first region.

9. The oximeter sensor of claim 8 wherein at least one of said first member and a second member is curved between said emitter and said detector to provide said lesser pressure.

10. The oximeter sensor of claim 1 further comprising an adhesive mounted on at least one of said first member and a second member for securely attaching said sensor to said tissue region.

11. The oximeter sensor of claim 1 wherein at least one of said attachment structure and said first member and a second member is configured to conform to the shape of said tissue region.

12. An oximeter sensor comprising:
    a first member configured to contact a first side of a tissue region of a patient;
    at least one emitter mounted in said first member;
    at least one detector mounted to contact said tissue region on a second side;
    an attachment structure configured to attach said sensor to said tissue region so that said detector is offset from a shortest path through said tissue region from said emitter; and
    a first diffuse or specular reflecting surface mounted to attach to said tissue region in a region of said offset;
    wherein said reflective surface comprises a partially reflective black and white pattern.

13. An oximeter sensor comprising:
    a first member configured to contact a first side of a tissue region of a patient;
    at least one emitter mounted in said first member;
    at least one detector mounted to contact said tissue region on said first side or a second side;
    an attachment structure configured to attach said sensor to said tissue region so that said detector is offset from a shortest path through said tissue region from said emitter; and
    a first diffuse or specular reflecting surface mounted to attach to said tissue region in a region of said offset;
    wherein said reflective surface reflects different amounts of light at each wavelength emitted by the emitter.

14. An oximeter sensor comprising:
    a first member configured to contact a first side of a tissue region of a patient;
    at least one emitter mounted in said first member;
    at least one detector mounted to contact said tissue region on said first side or a second side;
    an attachment structure configured to attach said sensor to said tissue region so that said detector is offset from a shortest path through said tissue region from said emitter;
    a first diffuse or specular reflecting surface mounted to attach to said tissue region in a region of said offset; and
    a second reflective surface mounted to said tissue region on an opposite side from said first reflective surface in a region of said offset.

15. An oximeter sensor comprising:
    a first member configured to contact a first side of a tissue region of a patient;
    at least one emitter mounted in said first member;
    wherein at least one emitter has a different offset distance to at least one other emitter;
    at least one detector mounted to contact said tissue region on said first side or a second side;
    an attachment structure configured to attach said sensor to said tissue region so that said detector is offset from a shortest path through said tissue region from said emitter; and
    a first diffuse or specular reflecting surface mounted to attach to said tissue region in a region of said offset.

16. A reflectance oximeter sensor comprising:
    a first member configured to contact a first side of a tissue region of a patient;
    at least one emitter mounted in said first member;
    at least one detector mounted on said first side of said tissue region;

an attachment structure configured to attach said sensor to said tissue region so that said emitter and said detector are offset from a shortest path through said tissue region said offset being at least twice said shortest path;

a first reflective surface mounted to attach to said tissue region in a region of said offset; and a second reflective surface mounted to said tissue region on an opposite side from said first reflective surface in a region of said offset.

17. An oximeter sensor comprising:

a first member configured to contact a first side of a tissue region of a patient;

at least one emitter mounted in said first member;

at least one detector mounted to contact said tissue region, on said first side or a second side of said tissue region, at a distance from said emitter that is greater than a shortest path through said tissue region from said emitter;

an attachment structure configured to attach said sensor to said tissue region;

a first reflective surface mounted to attach to said tissue region in region between said emitter and said detector; and a shunt barrier between said emitter and said detector in said first member.

18. The oximeter sensor of claim 17 further comprising:

a second reflective surface mounted to attach to said tissue region on an opposite side from said first reflective surface in-between said emitter and said detector.

19. An oximeter sensor comprising:

a first member configured to contact a first side of a tissue region of a patient;

at least one emitter mounted in said first member;

at least one detector mounted to contact said tissue region on said first side or a second side; and an attachment structure configured to attach said sensor to said tissue region so that said detector is offset from a shortest path through said tissue region from said emitter;

wherein at least one of said attachment structure and said first member is configured to apply less pressure to said tissue region in a first region between said emitter and said detector than a pressure applied to a second region of said tissue region outside said first region.

20. An oximeter sensor comprising:

a first member configured to contact a first side of a tissue region of a patient;

at least one emitter mounted in said first member;

at least one detector mounted to contact said tissue region on said first side or a second side;

an attachment structure configured to attach said sensor to said tissue region so that said detector is offset from a shortest path through said tissue region from said emitter;

a first diffuse or specular reflecting surface mounted to attach to said tissue region in a region of said offset; and a shunt barrier between said emitter and said detector in said first member.

21. An oximeter sensor comprising:

a first member configured to contact a first side of a tissue region of a patient;

at least one emitter mounted in said first member;

at least one detector mounted to contact said tissue region, on said first side or a second side of said tissue region, at a distance from said emitter that is at least twice as great as a shortest path through said tissue region from said emitter;

an attachment structure configured to attach said sensor to said tissue region; and a shunt barrier between said emitter and said detector in said first member.

* * * * *